United States Patent
Imaizumi et al.

(10) Patent No.: US 7,847,148 B2
(45) Date of Patent: Dec. 7, 2010

(54) OASIS GENE-DEFICIENT MOUSE

(75) Inventors: Kazunori Imaizumi, Miyazaki (JP); Shinichi Kondo, Miyazaki (JP); Akio Wanaka, Nara (JP)

(73) Assignee: University of Miyazaki, Miyazaki (JP)

( * ) Notice: Subject to any disclaimer, the term of this patent is extended or adjusted under 35 U.S.C. 154(b) by 0 days.

(21) Appl. No.: 12/281,321

(22) PCT Filed: Sep. 25, 2006

(86) PCT No.: PCT/JP2006/319628

§ 371 (c)(1),
(2), (4) Date: Aug. 30, 2008

(87) PCT Pub. No.: WO2007/102240

PCT Pub. Date: Sep. 13, 2007

(65) Prior Publication Data

US 2009/0019556 A1    Jan. 15, 2009

(30) Foreign Application Priority Data

Mar. 8, 2006  (JP) .............................. 2006-063197

(51) Int. Cl.
*A01K 67/027* (2006.01)
*A01K 67/00* (2006.01)
*A01K 67/033* (2006.01)

(52) U.S. Cl. .................. 800/18; 800/8; 800/9

(58) Field of Classification Search .................. 800/18, 800/8, 9

See application file for complete search history.

(56) References Cited

FOREIGN PATENT DOCUMENTS

JP    2005-052016 A    3/2005

OTHER PUBLICATIONS

Honma et al. Mol. Brain Res. 69:93-103; 1999.*
Yutaka Honma et al., "Identification of a novel gene, OASIS, which encodes for a putative CREB/ATF family transcription factor in the long-term cultured astrocytes andgliotic tissue", Molecular Brain Research 69 (1999) 93-103.
Tomohiko Murakami et al., "Cleavage of the membrane-bound transcription factor OASIS in response to endoplasmic reticulum stress", Journal of Neurochemistry, 2006, 96, 1090-1100.
Kazunori Imaizumi et al., "Saiboshu Tokuiteki Shohotai Stress Oto-astrocytes ni Hakken suru Shinki Shohotai Stress Sensor OASIS", Folia Pharmacol. Jpn. 2004, vol. 124, pp. 383 to 390.
Supplementary European Search Report for EP 06 81 0983 dated Jan. 12, 2010.
T. Nikaido et al., "Expression of the novel transcription factor OASIS, which belongs to the CREB/ATF family, in mouse embryo with special reference to bone development", Histochemistry and Cell Biology, (2001) 116:141-148.

* cited by examiner

*Primary Examiner*—Fereydoun G Sajjadi
(74) *Attorney, Agent, or Firm*—Stephen A. Bent; Foley & Lardner LLP

(57) ABSTRACT

A mouse that is deficient in the function of the gene for OASIS, and a method for screening for, or evaluating a pharmacological efficacy of, therapeutic agents for osteoporosis using the mouse.

1 Claim, 7 Drawing Sheets

Genome PCR

Genome Southern blot

SEQUENCE LISTING

```
<160> NUMBER OF SEQ ID NOS: 9

<210> SEQ ID NO 1
<211> LENGTH: 507
<212> TYPE: PRT
<213> ORGANISM: Mus musculus

<400> SEQUENCE: 1

Met Asp Ala Val Leu Glu Pro Phe Pro Ala Asp Arg Leu Phe Pro Gly
1               5                   10                  15

Ser Ser Phe Leu Asp Leu Gly Asp Leu Asn Glu Ser Asp Phe Leu Asn
            20                  25                  30

Asn Ala His Phe Pro Glu His Leu Asp His Phe Val Glu Asn Met Glu
        35                  40                  45

Asp Phe Ser Asn Asp Leu Phe Ser Ser Phe Phe Asp Asp Pro Val Leu
    50                  55                  60

Asp Glu Lys Ser Ala Leu Leu Asp Met Glu Leu Asp Ser Pro Ala Pro
65                  70                  75                  80

Gly Ile Gln Ala Glu His Ser Tyr Ser Leu Ser Gly Asp Ser Ala Pro
                85                  90                  95

Gln Ser Pro Leu Val Pro Val Lys Met Glu Asp Thr Thr Gln Asp Val
            100                 105                 110

Glu His Gly Ala Trp Ala Leu Gly Asn Lys Leu Cys Ser Ile Met Val
        115                 120                 125

Lys Gln Glu Gln Ser Pro Glu Leu Pro Val Asp Pro Leu Ala Ala Ser
    130                 135                 140

Ser Ala Met Ala Ala Ala Ala Met Ala Thr Pro Pro Leu Leu Gly
145                 150                 155                 160

Leu Ser Pro Met Pro Arg Leu Pro Ile Pro His Gln Ala Pro Gly Glu
                165                 170                 175

Met Thr Gln Leu Pro Val Ile Lys Ala Glu Pro Pro Glu Met Ser Gln
            180                 185                 190
```

-continued

```
Phe Leu Lys Val Thr Pro Glu Asp Leu Val Gln Met Pro Pro Thr Pro
        195                 200                 205
Pro Ser Ser His Gly Ser Asp Ser Asp Gly Ser Gln Ser Pro Arg Ser
    210                 215                 220
Leu Pro Pro Ser Ser Pro Val Arg Pro Met Ala Arg Ser Ser Thr Ala
225                 230                 235                 240
Ile Ser Thr Ser Pro Leu Leu Thr Ala Pro His Lys Leu Gln Gly Thr
                245                 250                 255
Ser Gly Pro Leu Leu Leu Thr Glu Glu Lys Arg Thr Leu Ile Ala
            260                 265                 270
Glu Gly Tyr Pro Ile Pro Thr Lys Leu Pro Leu Thr Lys Ala Glu Glu
        275                 280                 285
Lys Ala Leu Lys Arg Val Arg Arg Lys Ile Lys Asn Lys Ile Ser Ala
    290                 295                 300
Gln Glu Ser Arg Arg Lys Lys Lys Glu Tyr Val Glu Cys Leu Glu Lys
305                 310                 315                 320
Lys Val Glu Thr Tyr Thr Ser Glu Asn Asn Glu Leu Trp Lys Lys Val
                325                 330                 335
Glu Thr Leu Glu Thr Ala Asn Arg Thr Leu Leu Gln Gln Leu Gln Lys
            340                 345                 350
Leu Gln Thr Leu Val Thr Ser Lys Ile Ser Arg Pro Tyr Lys Met Ala
        355                 360                 365
Ala Thr Gln Thr Gly Thr Cys Leu Met Val Ala Ala Leu Cys Phe Val
    370                 375                 380
Leu Val Leu Gly Ser Leu Val Pro Cys Leu Pro Ala Phe Ser Ser Gly
385                 390                 395                 400
Ser Met Thr Val Lys Glu Asp Pro Ile Ala Ala Asp Ser Val Tyr Ala
                405                 410                 415
Ala Ser Gln Met Pro Ser Arg Ser Leu Leu Phe Tyr Asp Asp Gly Ala
            420                 425                 430
Gly Ser Trp Glu Asp Gly Arg Gly Ala Leu Leu Pro Val Glu Pro Pro
        435                 440                 445
Glu Gly Trp Glu Leu Lys Pro Gly Gly Pro Ala Glu Gln Arg Pro Gln
    450                 455                 460
Asp His Leu Arg His Asp Arg Ala Asp Ser Ile His Glu Thr Thr Lys
465                 470                 475                 480
Tyr Leu Arg Glu Thr Trp Pro Glu Asp Thr Asp Asn Gly Thr Ser
                485                 490                 495
Pro Asn Phe Ser His Pro Lys Gly Val Val Pro
            500                 505
```

<210> SEQ ID NO 2
<211> LENGTH: 1908
<212> TYPE: DNA
<213> ORGANISM: Mus musculus
<220> FEATURE:
<221> NAME/KEY: CDS
<222> LOCATION: (28)..(1551)

<400> SEQUENCE: 2

```
ggaaggggtc ccctggaacc cggcgcg atg gac gcc gtc ttg gaa cct ttc ccg    54
                            Met Asp Ala Val Leu Glu Pro Phe Pro
                             1               5 gcc gac agg ctg ttc ccg gga tcc agc ttc ctg gac ttg gga gac ctg    102
Ala Asp Arg Leu Phe Pro Gly Ser Ser Phe Leu Asp Leu Gly Asp Leu
 10              15                  20                  25
```

```
                                                         -continued aat gag tcg gat ttc ctc aac aat gcg cac ttc ccg gag cac ctg gac        150
Asn Glu Ser Asp Phe Leu Asn Asn Ala His Phe Pro Glu His Leu Asp
             30                  35                  40 cac ttt gtg gag aac atg gag gac ttc tcc aat gac ctg ttc agc agt        198
His Phe Val Glu Asn Met Glu Asp Phe Ser Asn Asp Leu Phe Ser Ser
                 45                  50                  55 ttc ttt gat gac cct gtg ctg gac gag aag agt gct ctg ctg gac atg        246
Phe Phe Asp Asp Pro Val Leu Asp Glu Lys Ser Ala Leu Leu Asp Met
         60                  65                  70 gaa ctg gac tcc ccc gct cca ggc atc cag gct gag cac agc tac tcc        294
Glu Leu Asp Ser Pro Ala Pro Gly Ile Gln Ala Glu His Ser Tyr Ser
     75                  80                  85 ctg agt ggg gat tct gca ccc cag agc ccc ctt gtg cct gtc aag atg        342
Leu Ser Gly Asp Ser Ala Pro Gln Ser Pro Leu Val Pro Val Lys Met
 90                  95                 100                 105 gag gac acc act caa gat gtg gaa cac gga gcg tgg gcc ctg gga aac        390
Glu Asp Thr Thr Gln Asp Val Glu His Gly Ala Trp Ala Leu Gly Asn
                110                 115                 120 aag ctg tgc tcc atc atg gtg aag cag gag cag agc ccg gag ctg cct        438
Lys Leu Cys Ser Ile Met Val Lys Gln Glu Gln Ser Pro Glu Leu Pro
            125                 130                 135 gta gat ccc ctg gct gcc tcc tct gcc atg gct gct gcc gcc gcc atg        486
Val Asp Pro Leu Ala Ala Ser Ser Ala Met Ala Ala Ala Ala Ala Met
        140                 145                 150 gcc acc cca cca ctg ctg ggc ctc agc ccc atg ccc cgg ctg ccc atc        534
Ala Thr Pro Pro Leu Leu Gly Leu Ser Pro Met Pro Arg Leu Pro Ile
    155                 160                 165 cct cac cag gcc cca gga gaa atg act cag ctg cca gtg atc aaa gca        582
Pro His Gln Ala Pro Gly Glu Met Thr Gln Leu Pro Val Ile Lys Ala
170                 175                 180                 185 gag ccc cca gaa atg agc cag ttt ctc aaa gtg aca cca gag gac ctc        630
Glu Pro Pro Glu Met Ser Gln Phe Leu Lys Val Thr Pro Glu Asp Leu
                190                 195                 200 gta cag atg cct cca aca ccc ccc agc agc cat ggc agt gac agt gac        678
Val Gln Met Pro Pro Thr Pro Pro Ser Ser His Gly Ser Asp Ser Asp
            205                 210                 215 ggc tcc cag agt ccc cgc tct ctt ccc ccc tcc agc cct gtc cgg ccc        726
Gly Ser Gln Ser Pro Arg Ser Leu Pro Pro Ser Ser Pro Val Arg Pro
        220                 225                 230 atg gcc cgc tcc tcc acg gcc att tcc acc tct ccg ctc ctc act gcc        774
Met Ala Arg Ser Ser Thr Ala Ile Ser Thr Ser Pro Leu Leu Thr Ala
    235                 240                 245 cct cac aaa ctg cag ggg aca tca ggg cca ctg ctc ttg aca gaa gag        822
Pro His Lys Leu Gln Gly Thr Ser Gly Pro Leu Leu Thr Glu Glu
250                 255                 260                 265 gag aag cgg acc ttg atc gcg gag ggt tac cct atc ccc acc aag ctc        870
Glu Lys Arg Thr Leu Ile Ala Glu Gly Tyr Pro Ile Pro Thr Lys Leu
                270                 275                 280 ccc ctc acc aag gct gag gag aag gcc ttg aag aga gta cgc agg aaa        918
Pro Leu Thr Lys Ala Glu Glu Lys Ala Leu Lys Arg Val Arg Arg Lys
            285                 290                 295 att aag aac aag att tct gcc cag gag agc cgc cgc aag aag aag gag        966
Ile Lys Asn Lys Ile Ser Ala Gln Glu Ser Arg Arg Lys Lys Lys Glu
        300                 305                 310 tat gtg gaa tgt cta gaa aag aag gtg gag aca tat aca tca gag aac       1014
Tyr Val Glu Cys Leu Glu Lys Lys Val Glu Thr Tyr Thr Ser Glu Asn
    315                 320                 325 aat gag ctg tgg aag aaa gtg gaa acc cta gag act gcc aac agg acc       1062
Asn Glu Leu Trp Lys Lys Val Glu Thr Leu Glu Thr Ala Asn Arg Thr
330                 335                 340                 345
```

```
ctg ctc cag cag ctg cag aaa ctc cag act ctg gtc acc agc aag atc    1110
Leu Leu Gln Gln Leu Gln Lys Leu Gln Thr Leu Val Thr Ser Lys Ile
            350                 355                 360 tcc aga ccg tac aag atg gca gcc acg cag acc ggc acc tgc ctc atg    1158
Ser Arg Pro Tyr Lys Met Ala Ala Thr Gln Thr Gly Thr Cys Leu Met
        365                 370                 375 gtg gca gcc ttg tgc ttc gtt ctg gtg ctg ggc tcc ctt gtc ccc tgc    1206
Val Ala Ala Leu Cys Phe Val Leu Val Leu Gly Ser Leu Val Pro Cys
                380                 385                 390 ctt cct gca ttc tct tcc ggc tca atg act gtg aaa gaa gac cct atc    1254
Leu Pro Ala Phe Ser Ser Gly Ser Met Thr Val Lys Glu Asp Pro Ile
395                 400                 405 gca gct gac agt gtc tat gca gcc agt cag atg cct tcc cga agc cta    1302
Ala Ala Asp Ser Val Tyr Ala Ala Ser Gln Met Pro Ser Arg Ser Leu
410                 415                 420                 425 ctg ttc tac gat gat ggg gca ggc tca tgg gaa gat ggc cga ggt gct    1350
Leu Phe Tyr Asp Asp Gly Ala Gly Ser Trp Glu Asp Gly Arg Gly Ala
                430                 435                 440 cta ctg cct gtg gag ccc cca gaa ggc tgg gag ctc aaa ccc ggg ggt    1398
Leu Leu Pro Val Glu Pro Pro Glu Gly Trp Glu Leu Lys Pro Gly Gly
            445                 450                 455 cca gca gag cag agg ccc cag gac cac ctc cga cat gac cgt gca gac    1446
Pro Ala Glu Gln Arg Pro Gln Asp His Leu Arg His Asp Arg Ala Asp
        460                 465                 470 agc atc cat gag acc acc aag tac ttg aga gag acc tgg cca gag gac    1494
Ser Ile His Glu Thr Thr Lys Tyr Leu Arg Glu Thr Trp Pro Glu Asp
    475                 480                 485 act gat gac aac ggc acc agc ccc aac ttc tcc cac ccc aag gga gtg    1542
Thr Asp Asp Asn Gly Thr Ser Pro Asn Phe Ser His Pro Lys Gly Val
490                 495                 500                 505 gtt cca tga cagggatctg ggccccaaca ccaccatcaa actctcctag             1591
Val Pro gccactccaa gaccaggaca caggacggac accctggcac ccagaagagg cgttctcttg  1651
ctcgatgacc cagatccagc tcatacccct gcccccgggg tccctgtagt agctggggac  1711
gctctatgtc cccagacact tggactgctc ccctgggctg accactccgt tcccaccttt  1771
ccctcctacc actatccgtc ctcctccgat aaaccactca ctgggctacc cgtttccttc  1831
ccatagtgac caacgcaacc actgttcctg gcccctcat acacaaacac acaagcagac   1891
atacacacac aaacaca                                                 1908

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gcggccgccc acagacaaca ggcatacaca agg                                33

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
```

```
ctcgagtcac tccgggaagt gctggggagg ga                                    32

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gaattccagg acagccaggg ctac                                             24

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gaattcgctg agctaatcct ggagactctc                                       30

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ccctctccaa gcctcactga gg                                               22

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
taccctgctg taagggctt gtgg                                              24

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tccatcttgt tcaatggccg atcc                                             24
```

OASIS GENE-DEFICIENT MOUSE

TECHNICAL FIELD

The present invention relates to a mouse deficient in an OASIS gene, more specifically an osteoporosis model mouse. The present invention also relates to a method for screening for therapeutic agents for osteoporosis using said mouse.

BACKGROUND ART

It has become clear that endoplasmic reticulum stress participates deeply in the onset of various intractable diseases, such as neurodegenerative diseases and diabetes. The present inventors have previously discovered a novel transcription factor localized in the endoplasmic reticulum, OASIS (Old Astrocyte Specifically-Induced Substance), which plays an important role in signaling to avoid the endoplasmic reticulum stress (Japanese Patent Publication (Kokai) No. 2005-52016A).

The OASIS protein is a one transmembrane type basic leucine zipper (bZIP) transcription factor belonging to a CREB (Cyclic AMP Response Element Binding protein)/ATF(Activating Transcription Factor) family, and its gene was identified as a gene expressed specifically in murine astrocytes after long-term culture, and the sequences of the gene and the protein have been analyzed (Honma Y. et al., Molecular Brain Research, 69: 93-103, 1999). Thereafter, the human-derived OASIS gene was isolated, whose nucleotide sequence and the amino acid sequence encoded thereby were both identified (Omori Y. et al., Biochem Biophysic Res Commun, 26: 293 (1): 407-7 (2002)).

The present inventors have previously discovered that, although the OASIS protein exists in a normal status on the endoplasmic reticulum membrane of glial cells, when endoplasmic reticulum stress is loaded on the glial cell, the OASIS protein is cleaved by the phenomenon of RIP (Regulated Intramembrane Proteolysis) in the membrane (Brown, M. S. et al., Cell, 100, 391-398, 2000); the cleaved fragments (containing a basic leucine zipper (bZIP) common in CREB/ATF transcription factors) are transported into the nucleus; and in the nucleus the cleaved fragments bind to ERSE (ER Stress Response Element) and CRE (Cyclic AMP Response Element) (Mori, K., Cell, 101, 451-454, 2000), thereby inducing the expression of GRP78, an ER stress resistant chaperone, and the like, and promoting the activation or expression of the OASIS protein, and as a result, the death of nerve cells caused by the ER stress can be inhibited, or neurodegenerative diseases may be cured (Japanese Patent Publication (Kokai) No. 2005-52016A).

DISCLOSURE OF THE INVENTION

The present inventors tried to generate an OASIS gene-deficient (or knockout) mouse in order to understand the in vivo role and function of the OASIS protein.

An object of the present invention is to generate an OASIS-deficient mouse, and to clarify its characteristics.

Another object of the present invention is to use the OASIS gene-deficient mouse for the screening of therapeutic agents, or for the evaluation of a pharmacological effect of the agents.

SUMMARY OF THE INVENTION

The present inventors have now surprisingly found that the generated mouse exhibited a lesion quite similar to osteoporosis.

In the first aspect, the present invention provides a mouse in which the function of the gene for OASIS, a transcription factor localized in the endoplasmic reticulum, is deficient.

In one embodiment, the mouse of the present invention is characterized by being an osteoporosis model mouse.

In another embodiment, the mouse of the present invention has properties of a reduced body weight, deformed limbs, and a reduced bone mass, as compared with a wild type thereof.

In the second aspect, the present invention provides a method for screening candidate agents for therapeutic agents for osteoporosis, comprising administering a candidate agent to the mouse according to the present invention.

In the third aspect, the present invention provides a method for evaluating a pharmacological effect of a therapeutic agent for osteoporosis, comprising administering the therapeutic drug for osteoporosis to the mouse according to the present invention.

DEFINITION

The term "deficient in function" as used herein means that all or part of the OASIS gene on the wild type mouse genome is modified (for example substituted, deleted, added and/or inserted) or disrupted, whereby the expression product of the gene does not exhibit the function of the OASIS protein, or the protein is not expressed. Such mouse is also called herein as an OASIS gene-deficient mouse or an OASIS gene-knock-out mouse.

The term "osteoporosis" as used herein means a disease or symptom, in which bone mass decreases thereby making the bones weak and fragile and the bones become susceptible to fracture. Structurally, the decrease in bone mass in the spongy bone is more remarkable than in the cortical bone, resulting in reduction of trabecular bone, which makes bones weak. Since the bone metabolism occurs more actively in the spongy bone than in the cortical bone, by incidence of abnormality in the bone metabolism, a change happens initially in the spongy bone to reduce the bone mass of spongy bone. At the onset of osteoporosis, the backbone, which is relatively rich in spongy bone, tends to become weak earlier. Further, deformed limbs are observed as one of the symptoms in the mouse according to the present invention, which is recognized as a typical symptom in the secondary osteoporosis (e.g. rheumatoid arthritis).

The term "wild type" as used herein refers to a mouse having a normal OASIS gene.

The contents described in the description and/or the drawings of Japanese Patent Application No. 2006-063197, to which this application claims priority, are incorporated by reference herein in its entirety.

BRIEF DESCRIPTION OF THE DRAWINGS

FIG. 1 illustrates generation of an OASIS knockout mouse.

DETAILED DESCRIPTION OF THE INVENTION

1. OASIS Gene-Deficient Mouse

A mouse deficient in OASIS gene according to the present invention is a so-called knockout mouse, whose OASIS gene on the genome is deleted or dysfunctioned. More specifically, a part of the genomic DNA of the OASIS gene is modified by deletion, substitution, addition or insertion, so that the function of the gene is completely or substantially impaired or lost. Due to deficiency in the gene, the OASIS gene is not expressed, and consequently the OASIS protein is not synthesized and is unable to function in vivo. In case the protein should bear an important role in vivo, it is expected that a morbid symptom would appear by disturbing the development and growth processes of the mouse.

The mouse deficient in OASIS gene according to the present invention has the following characteristics.

Figure 3:
FIG. 3 shows a photograph of the 12-week old wild type male mouse 2F-M2 (OASIS +/+; body weight 29.88 g; and body length 9.0 cm) and the OASIS-knockout mouse 2F-M3 (OASIS −/−; body weight 24.33 g; and body length 8.0 cm).
Figure 4:
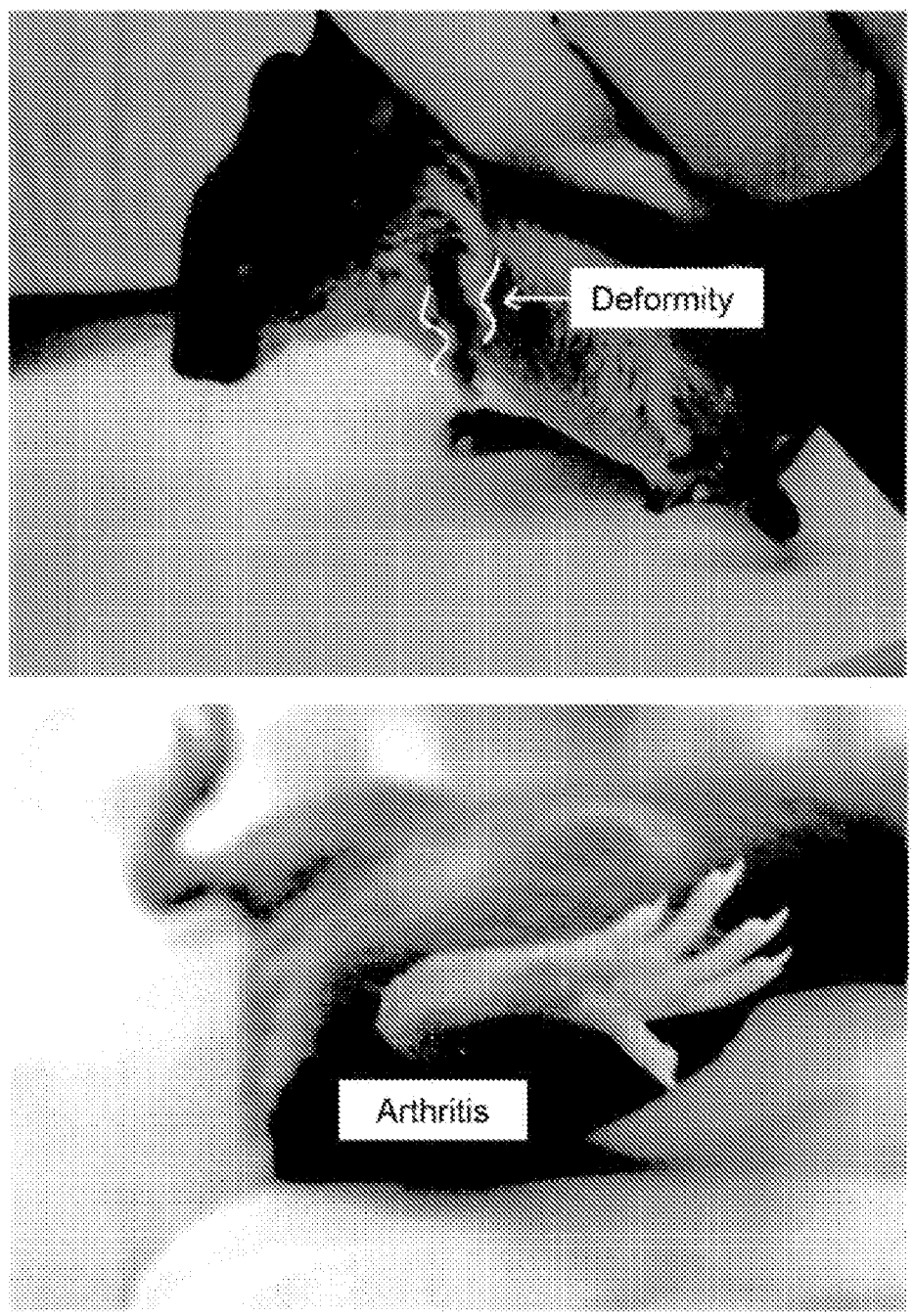
FIG. 4 illustrates a naked eye-observable lesion of an 8-week old OASIS-knockout mouse. In the upper panel, deformity of a forelimb is observed. In the lower panel, arthritis and rubefacient swelling are observed at the heel of a hindlimb.

Namely, the mouse according to the present invention has such characteristics that decrease in body weight is recognized from about 2 weeks after birth (FIG. 2); deformity of the limbs or changes, such as rubefacient swelling, at and around a joint (due to a fracture) are recognized by observation with the naked eye (FIGS. 2 and 3); a lesion of osteoporosis, such as remarkable reduction in bone masses of the long bone and the spongy bone, is recognized as the result of a histopathological analysis (FIG. 4).

Since the mouse according to the present invention exhibits a very similar lesion as osteoporosis, it is useful as an osteoporosis model mouse. Although it was known that OASIS is useful in treating a neurodegenerative disease owing to its protection effect from, for example, the death of nerve cells caused by ER stress (Japanese Patent Publication (Kokai) No. 2005-52016 A, the relationship of OASIS with osteoporosis or osteogenesis was not known at all. Such characteristics were not known until before the successful generation of the OASIS gene-deficient mouse by the present inventors.

The mouse according to the present invention can generally be generated using known gene targeting methods (for example, Methods in Enzymology, 225: 803-890, 1993).

The respective sequences of the murine OASIS protein and the DNA coding for same are registered in GenBank under NM_011957, and are shown in the sequence listing described later, as SEQ ID NO: 1 and SEQ ID NO: 2, respectively. A probe (e.g. about 30 to 150 bases in length) is prepared based on the nucleotide sequence, and then labeled with a radioactive or fluorescent label, and the resulting labeled probe can be used for detecting or isolating the genomic DNA of the OASIS gene. The genomic DNA is removed from cells derived from tissues such as brain and tail, according to conventional methods, the genomic DNA is digested with restriction enzymes, and the open reading frame (ORF) of the target OASIS gene is searched by a hybridization method using the aforedescribed probe, such as Southern hybridization or in situ hybridization. Optionally, a restriction map is prepared, and any target site for homologous recombination is determined. Genomic DNA fragment containing the OASIS gene is amplified by polymerase chain reaction (PCR) using primers (e.g. about 15 to 25 bases in length) prepared based on the nucleotide sequence of the OASIS gene, and the sequence of the fragment is partially determined. The size of homologous regions for homologous recombination is preferably about 3 to 7 kb or longer.

Figure 1A:
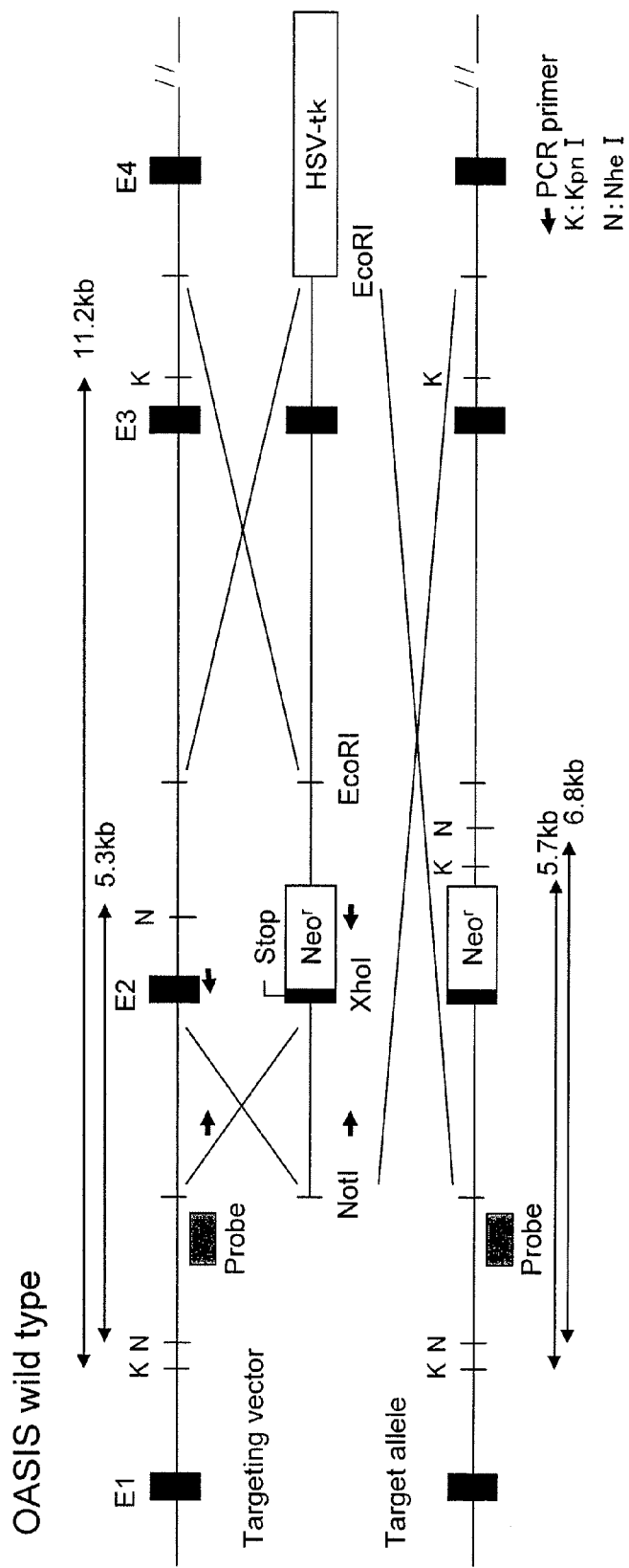
FIG. 1a illustrates the construction of a targeting vector. E1, E2, E3 and E4 represent Exon 1, Exon 2, Exon 3 and Exon 4 of the OASIS gene, respectively. Neo$^r$ stands for a neomycin-resistant gene, and HSV-tk for an HSV thymidine kinase gene, respectively.

To knockout the OASIS gene, the homologous region in a targeting vector may be inserted or substituted with a foreign DNA, such as a drug resistance gene (for example, neomycin-resistant gene, or hygromycin B phosphotransferase gene), or a part of the OASIS gene may be deleted. The site of deletion or the site of insertion or substitution with a foreign DNA is, for example, at any one of exons of the OASIS gene, e.g. Exon 2 (E2 in FIG. 1). The drug resistance gene as a foreign DNA is useful for positive selection of an embryonic stem cell having the targeting vector. The vector may be introduced with a gene for negative selection, wherein examples of the gene include HSV thymidine kinase (HSV-tk) gene and diphtheria toxin A gene. Negative selection is useful for selecting an embryonic stem cell with integrated random vector susceptible to drugs, such as an antiherpes drug, FIAU and ganciclovir.

Examples of a vector that can be selected as a targeting vector include pGT-N28 (New England BioLabs), pBluescript II SK+ (Stratagene), pSP72, and pPNT.

For higher efficiency of the homologous recombination, for example, a Cre-loxP system (R. Kuhn, et al., Science, 1995, 269: 1427-1429) may be utilized (see below).

To generate the mouse according to the present invention, a method that the vector DNA is directly injected into a murine fertilized egg, which is then transplanted to a surrogate mother, may be applicable, but a method using a murine embryonic stem (ES) cell is preferable.

The ES cell is a cell line that grows continuously keeping an undifferentiated state, which is established by culture of undifferentiated cells from an inner cell mass existing in the blastocyst after fertilization or in an 8-cell-stage embryo, by repeating dissociation of a cell mass and subculturing. Examples of a murine ES cell line include, but are not limited to, D3 cell line, E14TG2a cell line, TT2 cell line, AB-1 cell line, J1 cell line and R1 cell line.

A targeting vector, in which the OASIS gene is altered to lose the function as described above, is introduced into a murine ES cell according to known methods. Examples of the introduction methods include, but are not limited to, a microcell method, an electroporation method, a liposome method, a calcium phosphate method, and a DEAE-dextran method.

The obtained recombinant ES cells may be screened for successful homologous recombination by, for example, a Southern blotting method or a genome PCR method using a probe or primers respectively. As such, a cell, in which a correct homologous recombination has taken place, is selected.

An OASIS gene-knockout ES cell is introduced into a blastocyst or an 8-cell-stage embryo of a wild type mouse.

Then the embryo containing the ES cell is transplanted into the uterus of a pseudopregnant surrogate mother mouse for delivery, to produce a chimeric animal.

As a method for introducing an ES cell into an embryo, such as blastocyst, micro-injection and condensation methods are known, either of which can be utilized. In case of a mouse, a female mouse treated with a hormone for overovulation is mated with a male mouse to obtain an embryo in early development. When the blastocyst is used as an embryo to introduce a recombinant ES cell(s), an embryo in early development is recovered from the uterus on day 3.5 of fertilization, and when an 8-cell-stage embryo is used, on day 2.5. The ES cell subjected to homologous recombination using said targeting vector is injected in vitro into the thus recovered embryo to produce a chimeric embryo.

On the other hand, a pseudopregnant female mouse used as a surrogate mother can be prepared by mating a female mouse having a normal sexual cycle with a male mouse castrated by vasoligation or the like. The chimeric embryo produced by the above method is transplanted into the uterus of the prepared pseudopregnant mouse, which then becomes pregnant and gives a birth to generate a chimeric mouse. It is preferable to prepare a female mouse, from which a fertilized ovum is collected, and the pseudopregnant female mouse as a surrogate mother should be selected from a group of female mice having an identical sexual cycle for the sake of higher assurance of success in implantation and pregnancy of the chimeric embryo.

When mouse individuals derived from the ES cell transplanted embryo are obtained from among said chimeric mice, the chimeric mouse can be mated with a pure line mouse. If the coat color originated from the ES cell appears among the second generation individuals, introduction of the ES cell into the germ line of the chimeric mouse can be verified. Various indices can be utilized to verify the introduction of an ES cell into the germ line, but a coat color is preferable owing to easiness in verification. It is also possible to extract DNA from a part of the body (e.g. tail) for screening by conducting Southern blot analysis or PCR assay.

Animals, in which an ES cell introduced into an embryo has been transplanted into the germ line, are selected as above, and the resulting chimeric animals are bred to obtain individuals deficient in a target gene. By mating each other the obtained heterozygous mice (+/−) deficient in the OASIS gene, or by mating the chimeric mouse with a wild type mouse, a homozygous mouse (−/−) deficient in the target gene can be obtained. The produced heterozygote or homozygote having a modified OASIS gene owns the OASIS gene deficiency stably in all of the germ cells and somatic cells and such gene deficiency is genetically transferred to the offspring animals. The mouse according to the present invention therefore includes both the chimeric mice deficient in the function of the OASIS gene and the offspring mice having same deficiency.

To produce the knockout mouse of the present invention, the Cre/loxP system (R. Kuhn, et al., Science, 1995, 269: 1427-1429), being used in producing a knockout mouse, can also be used. With the Cre/loxP system, an OASIS gene deficient mouse having a gene, in which a foreign DNA sequence flanked by loxP sequences has been inserted into a target homologous sequence, is mated with an animal expressing a Cre enzyme, which is a recombination enzyme derived from P1 phage of E. coli, to produce an animal, in which the Cre enzyme recognizes the sequence flanked by the loxP sequences and delete the same, thereby making it possible to produce an animal deficient in the region. With the Cre/loxP system, it is possible to produce a knockout mouse characterized by a tissue-specific gene deficiency, by mating with a mouse expressing a Cre enzyme tissue-specifically.

Specific procedures concerning gene targeting may be, for example, referred to "Gene targeting-Generation of mutant mouse using ES cell", Bio-manual Series 8 (Yodosha, Tokyo, Japan), written by Aizawa Shinichi (1995).

Figure 2:
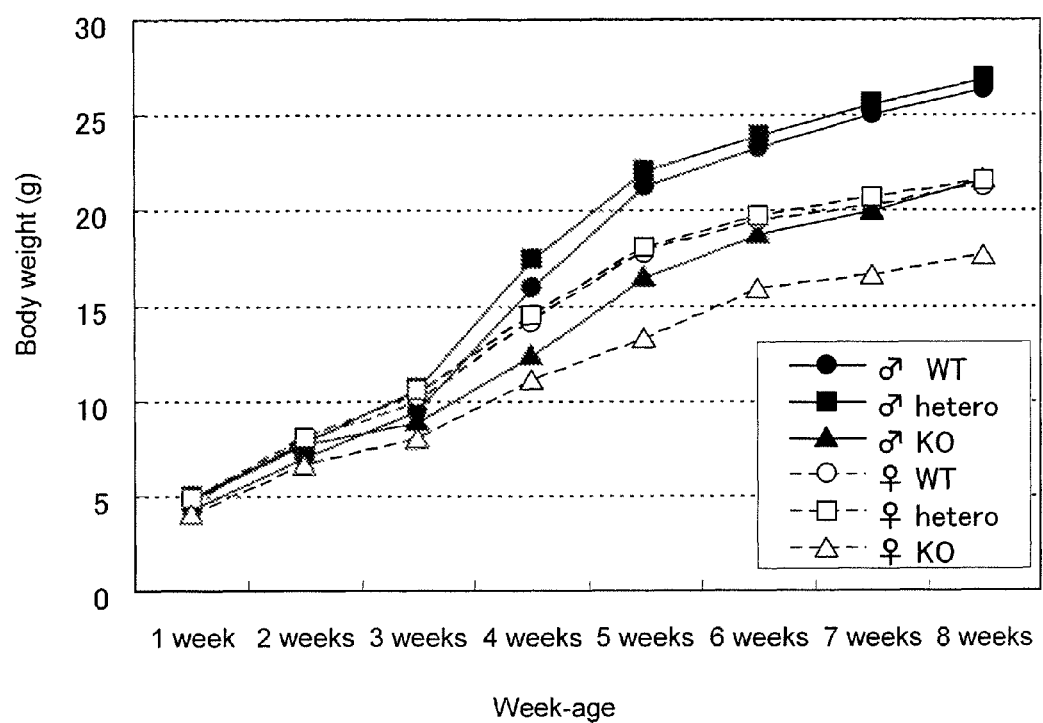
FIG. 2 illustrates changes in body weight of the OASIS-knockout mouse (KO) after the first week of birth. In this figure, WT stands for a wild type mouse, and hetero for a heterozygous mouse respectively.
Figure 6:
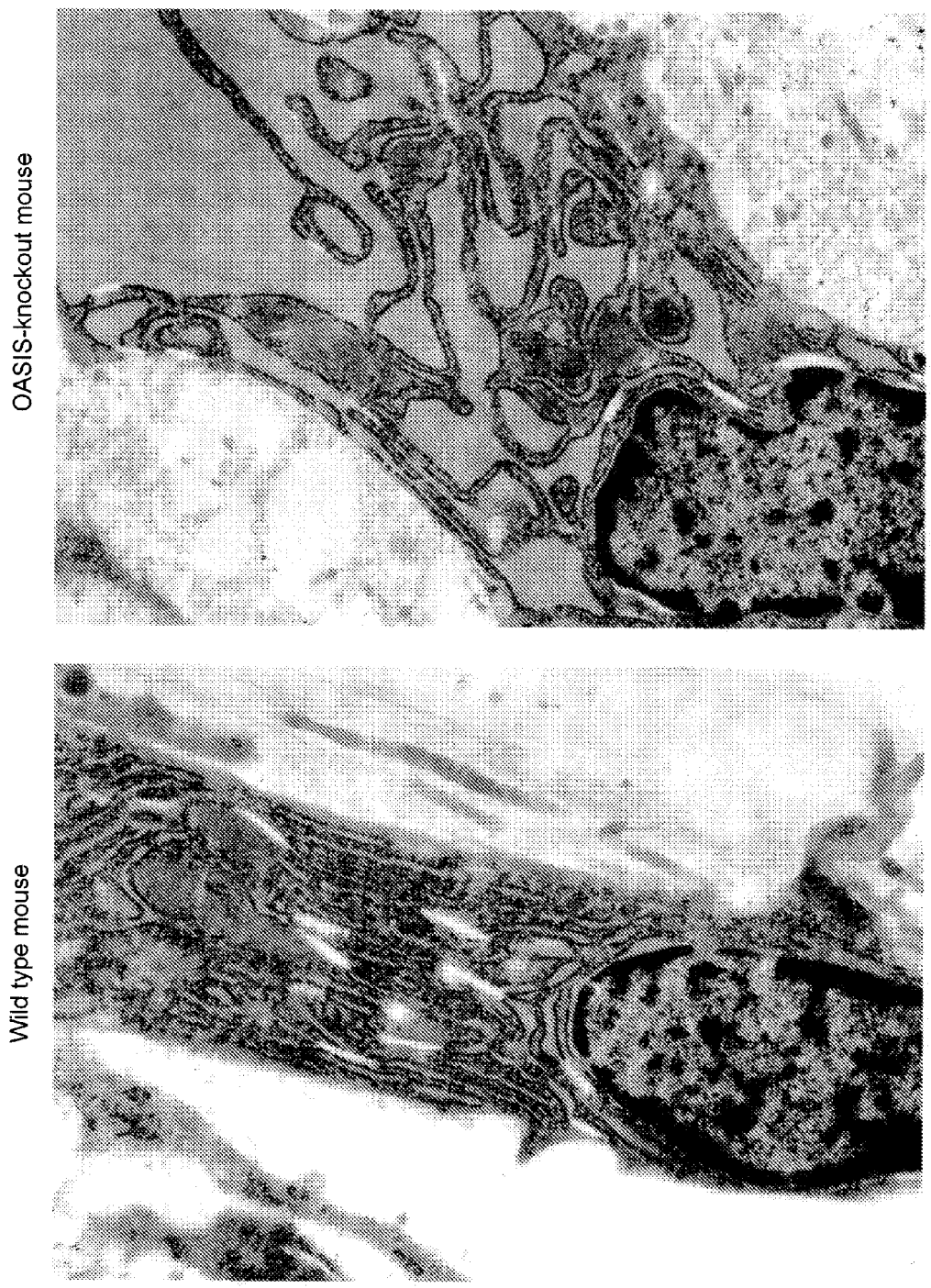
FIG. 6 shows electron-microscopic photographs of osteoblasts of the wild type mouse (left) and the OASIS knockout mouse (right).

2. Screening of Therapeutic Agents for Osteoporosis and Evaluation of Pharmacological Effect With the OASIS gene-deficient mouse according to the present invention, the bone mass of spongy bone is remarkably reduced compared to the wild type mouse, and as a result, bone fractures are observed in the limbs and the vertebra (FIGS. 2 to 4). By electron-microscopic observation on osteoblasts of the OASIS knockout mouse, the remarkable expansion of endoplasmic reticulum and the accumulation of substances with high electron density in the lumen of endoplasmic reticulum have now been found, which findings confirmed that the bone lesion in the KO mouse was surely caused by dysfunction of endoplasmic reticulum (FIG. 6). Thus, said findings reveal that the OASIS gene is closely associated with the osteogenesis and the deficiency in the gene caused a lesion very similar to human osteoporosis.

Therefore, the mouse according to the present invention can be used as an osteoporosis model mouse. More specifically, the mouse according to the present invention can be used to screen therapeutic agents for osteoporosis or to evaluate a pharmacological effect thereof, or as a tool for analyzing a pathogenic mechanism of osteoporosis or a tool for clarifying a molecular mechanism of ER stress response.

In the second aspect, the present invention provides a method for screening candidate agents for a therapeutic agent for osteoporosis, comprising administering a candidate agent to the mouse according to the present invention.

In the third aspect, the present invention provides a method for evaluating a pharmacological effect of a therapeutic agent for osteoporosis, comprising administering the therapeutic agent for osteoporosis to the mouse according to the present invention.

Candidate agents include, but are not limited to, small molecules, (poly)peptides, (glyco)proteins, (poly)nucleotides, nucleic acids, nucleosides, glucides and lipids, etc. Examples of candidate agents include the OASIS protein, modified derivatives thereof (e.g. pegylated, acylated, alkylated, phosphorylated or sulfated derivatives), OASIS homologs and modified derivatives thereof, etc.

Examples of therapeutic agents for osteoporosis include, but are not limited to, female hormones, calcitonin, bisphosphate, ipriflavone, vitamin K2 and vitamin D3.

Methods of administration of a candidate agent or therapeutic agent include, but are not limited to, oral administration and parenteral administration (e.g. intravenous administration, intraperitoneal administration and intranasal administration). In case of oral administration a candidate agent may be blended in a feed for administration.

Although there is no restriction, the dose is in the range of about 1 μg to 100 mg.

The candidate agent or therapeutic agent may be administered in combination with a pharmaceutically acceptable conventional excipient (such as carrier and diluent) or additives, Further, the candidate agent or therapeutic agent may be encapsulated in, or bound (or attached) to, liposomes (e.g. positively charged liposomes) or nano-particles and administered.

Evaluation can be conducted using mitigation or recovery of osteoporosis symptoms, increase in bone mass of spongy bone, increase in body weight, recovery from deformity of limbs, or the like, as an indication, by observation with naked eye, measurement of body weight, histopathological observation (e.g. microscopic observation after tissue staining) and the like (see Examples below).

The present invention will now be described in more detail by working examples, provided that the examples should not be interpreted as those limiting the scope of the present invention.

EXAMPLES

Example 1

Preparation of Targeting Vector

Using primers prepared based on the murine OASIS genome sequence (ENSMUSG00000027230) and a genomic DNA derived from a 129 mouse as a template, a PCR was carried out to isolate DNA fragments, upstream and downstream of Exon 2 of the OASIS gene, sized 1.5 kb (short arm) and 6 kb (long arm). The primers used for the short arm side were 5'-GCGGCCGCCCACAGACAACAGGCATACA-CAAGG-3' (SEQ ID NO: 3) and 5'-CTCGAGTCACTC-CGGGAAGTGCTGGGGAGGGA-3' (SEQ ID NO: 4), and for the long arm side were 5'-GAATTCCAGGACAGC-CAGGGCTAC-3' (SEQ ID NO: 5) and 5'-GAATTCGCT-GAGCTAATCCTGGAGACTCTC-3' (SEQ ID NO: 6). After confirming by sequencing that base substitution had not occurred, the respective DNA fragments were inserted into a NotI-XhoI site (short arm) and a EcoRI-EcoRI site (long arm) of a targeting vector pPNT (kindly gifted by the author of: Cell, 1991 Jun. 28, 65 (7): 1153-1163, Dr. Masaru Okabe (Osaka University, Osaka, Japan)), to construct the targeting vector (see FIG. 1a).

Example 2

Generation of OASIS Knockout Mouse

The targeting vector of Example 1 was introduced by an electroporation method into cultured undifferentiated murine ES cells (approximately $0.8 \times 10^7$ cells), D3 cell line (Doetschman et al., J Embryol Exp Morphol, 1985, 87: 27-45) at the rate of 25 μg/mL to obtain transgenic ES cells. The cells were seeded on a plate (ESM medium), after 24 hours G418, and after 48 hours G418 and ganciclovir were added to the medium, and the culture was continued for additional 7 to 10 days to obtain colonies resistant to G418 and ganciclovir. Individual colonies were separated and further cultured, and then the DNAs were extracted to select homologous recombinant ES cells by Southern blotting.

Next, the homologous recombinant ES cell was injected into the blastocyst of a C57BL/6CR SLC strain mouse according to the conventional method, which cell was then transplanted to a surrogate mother mouse to develop to an individual. As a result, 2 chimeric mice were obtained. Out of the obtained chimeric mice, a male individual was mated with a female wild type C57B/6 strain mouse to obtain the first generation ($F_1$) mice. Individuals (male, female), in which the modified sequence was detected in either of diploid chromosomes, were selected out of the $F_1$ mice by Southern blot analysis, and they were mated to obtain the second generation ($F_2$) mice.

Figure 1B:
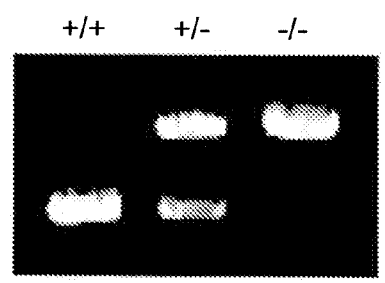
FIG. 1b illustrates confirmation of the deficiency in OASIS gene by genome PCR, wherein +/+ is a wild type mouse, +/− is a heterozygous mouse, and −/− is a knockout mouse.
Figure 1C:
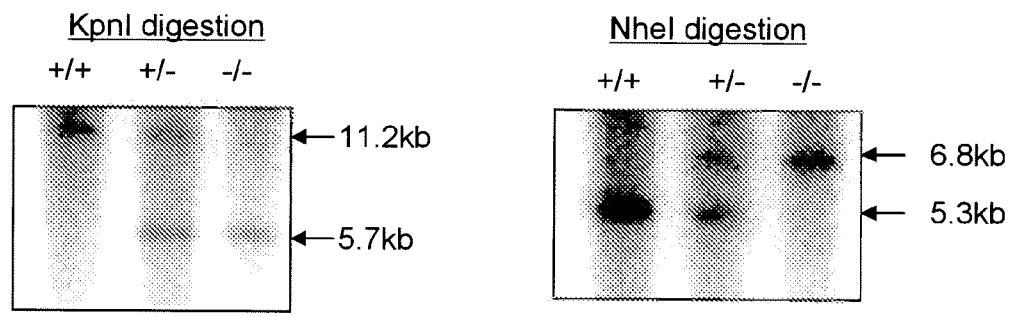
FIG. 1c illustrates Southern blots of the OASIS gene digested separately by KpnI and NheI. With the OASIS gene-knockout genome, a band of 5.7 kbp by the KpnI digestion, and a band of 6.8 kbp by the NheI digestion were respectively detected.

As the result of a genome PCR using primers of 5'-CCCTCTCCAAGCCTCACTGAGG-3' (SEQ ID NO: 7), 5'-TACCCTGCTGTAAGGGGCTTGTGG-3' (SEQ ID NO: 8) and 5'-TCCATCTTGTTCAATGGCCGATCC-3' (SEQ ID NO: 9), the deficiency of the OASIS gene in the knockout mouse (−/−) was confirmed (see FIG. 1b). Further, as FIG. 1c shows, when the OASIS gene in the knockout genome was digested by KpnI or NheI and analyzed by Southern blotting, in case of the KpnI digestion a band of 5.7 kbp, and in case of the NheI digestion a band of 6.8 kbp were detected respectively. The results indicated that the homologous recombination in the OASIS gene took place successfully and that an OASIS gene knockout mouse was generated successfully.

Example 3

Characterization of OASIS Knockout Mouse

Change in Body Weight

Body weight was measured from week 1 of birth to week 8 to observe changes over time for male and female mice of the wild type (WT), heterozygote (hetero) and homozygote (KO).

The results are shown in FIG. 2. The figure shows that the increase of the body weight of a knockout mouse (KO) and a heterozygous mouse according to the present invention was significantly reduced from about week 3 after birth in comparison with the wild type, and the increase of the body weight of a female knockout mouse was most severely suppressed. It revealed that knockout of the OASIS gene caused abnormality in osteogenesis, resulting in suppression of the increase in body weight.

Observation with the Naked Eye

The body length and the body weight of the wild type mouse and the knockout mouse according to the present invention, both 12-week old, were measured and compared.

The results are shown in FIG. 3. As shown in the figure, the body weight and the body length of the wild type were 29.88 g and 9.0 cm respectively, while the body weight and the body length of the knockout mouse were 24.33 g and 8.0 cm respectively. In other words, both the body length and the body weight of the OASIS gene knockout mouse were smaller or lower than those of the wild type mouse, which was responsible for the reduction in bone mass caused by abnormality in osteogenesis.

Furthermore, the lesion of an 8-week old OASIS knockout mouse was visually observed. As a result, deformity in the forelimb was observed (FIG. 4, upper panel). Further, arthritis and rubefacient swelling at the heel of a hindlimb were observed (FIG. 4, lower panel). The rubefacient swelling was found to having been caused by bone fracture.

Histopathological Observation of Bone Lesion in Vertebra

The bone mass of the vertebra was compared between the wild type mouse and the OASIS knockout mouse. Tissue samples of vertebrae were taken, decalcified by treatment with formic acid, prepared to paraffin sections according to the conventional method, and stained with hematoxylin-eosin. The bone lesion was microscopically observed.

Figure 5:
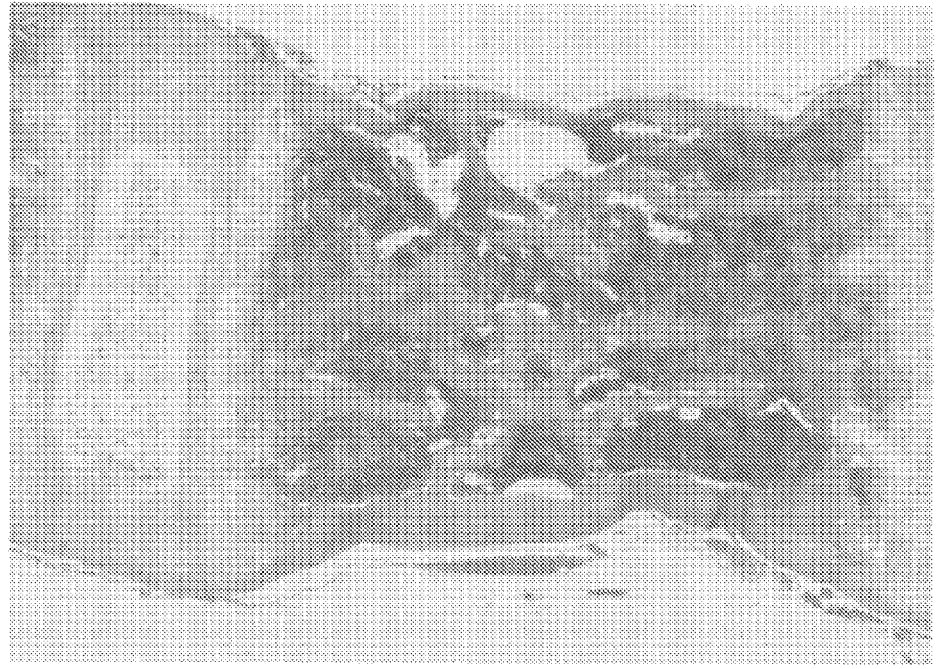
FIG. 5 shows a histological staining with hematoxylin-eosin (HE) comparing bone masses in the vertebrae of the wild type mouse (left) and the OASIS knockout mouse (right).
Figure 5:
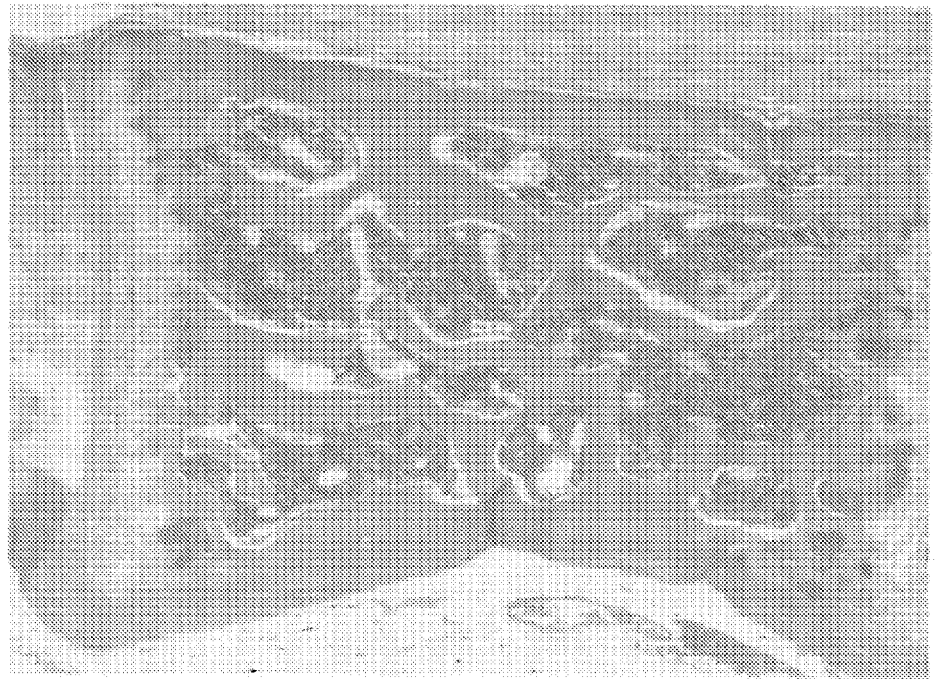

The results are shown in FIG. 5. As seen in the figure, the bone mass in the long bone and spongy bone was remarkably decreased in the OASIS knockout mouse (right panel) in comparison to the wild type mouse (left panel). Further, bone fractures in the vertebra and limbs were recognized. It was known that OASIS expresses in an osteoblast (Honma Y. et al., Molecular Brain Research, 69: 93-103, 1999). So, osteoblast was observed electron-microscopically for its hyperfine structure.

The results are shown in FIG. 6. As seen in the figure, with respect to the osteoblast of the OASIS knockout mouse (right panel) in comparison to the wild type mouse (left panel), endoplasmic reticulum was remarkably expanded, and substances with high electron density were accumulated in the lumen of endoplasmic reticulum. The electron-microscopic observation shows that the bone lesion in the KO mouse was surely caused by dysfunction of the endoplasmic reticulum.

The above findings revealed that the OASIS gene was closely associated with osteogenesis, and that the deficiency in the gene caused a lesion very similar to human osteoporosis.

The present invention provides an osteoporosis model mouse accordingly. Since the use of the mouse of the present invention enables, regarding osteoporosis, development of therapeutic agents and evaluation of a pharmacological effect of the agents, analysis of a pathogenic mechanism, study on the molecular mechanism of an ER stress response, and the like, the mouse is very useful in the industry.

INDUSTRIAL APPLICABILITY

According to the present invention, it has been found that the OASIS gene is closely associated with osteogenesis. It has been further found that deficiency in the gene causes a lesion very similar to human osteoporosis. Therefore, the mouse of the present invention provides significant advantages of its use as an osteoporosis model mouse.

All publications, patents and patent applications are incorporated by reference herein in their entirety.

Sequence Listing Free Text

SEQ ID NO: 3: primer
SEQ ID NO: 4: primer
SEQ ID NO: 5: primer
SEQ ID NO: 6: primer
SEQ ID NO: 7: primer
SEQ ID NO: 8: primer
SEQ ID NO: 9: primer

What is claimed is:

1. A transgenic mouse whose genome comprises a homozygous functional disruption of the endogenous OASIS (Old Astrocyte Specifically-Induced Substance) gene encoding a transcription factor, which mouse exhibits, relative to a wild type mouse, a phenotype that is characterized by deformed limbs and reduced spongy bone mass.

* * * * *